United States Patent [19]
Scharbach et al.

[11] 3,987,499
[45] Oct. 26, 1976

[54] SURGICAL IMPLANT AND METHOD FOR ITS PRODUCTION

[75] Inventors: Heinz Scharbach, Plankstadt; Achim Engelhardt; Peter Bunz, both of Frankfurt, all of Germany

[73] Assignee: Sybron Corporation, Rochester, N.Y.

[22] Filed: Aug. 9, 1974

[21] Appl. No.: 496,268

[30] Foreign Application Priority Data
Aug. 10, 1973  Germany.............................. 2340546

[52] U.S. Cl.................................. 3/1.91; 3/1.913; 3/1.9; 128/92 B; 128/92 D; 128/92 C; 128/92 CA
[51] Int. Cl.² ......................................... A61F 1/24
[58] Field of Search ............................ 3/1.9–1.913, 3/1; 128/92 C, 92 CA, 92 R, 92 B, 92 D; 32/10 A; 106/48

[56] References Cited
UNITED STATES PATENTS

| | | | |
|---|---|---|---|
| 2,696,817 | 12/1954 | Prevo................................. | 128/92 C |
| 3,067,740 | 12/1962 | Haboush ......................... | 128/92 CA |
| 3,368,712 | 2/1968 | Sanford et al. ....................... | 220/64 |
| 3,397,076 | 8/1968 | Little .................................... | 106/48 |
| 3,426,364 | 2/1969 | Lumb..................................... | 3/1 |
| 3,658,056 | 4/1972 | Huggler et al.................. | 128/92 CA |
| 3,707,006 | 12/1972 | Bokros et al..................... | 32/10 A X |
| 3,717,932 | 2/1973 | Brainin ............................... | 32/10 A |

FOREIGN PATENTS OR APPLICATIONS

| | | | |
|---|---|---|---|
| 1,099,519 | 3/1955 | France ............................ | 128/92 CA |

OTHER PUBLICATIONS

"The Deterioration of Materials In Use" by D. F. Williams, *Implants In Surgery* (Book) by Williams and Roaf, W.B. Saunders Co. Ltd. publisher, London, Philadelphia, Toronto, published, July 3, 1973, pp. 158, 174 and 175 relied upon.

"A Femoral-Head Prosthesis for the Hip Joint" by E.D. McBride, *The Journal of Bone and Joint Surgery*, vol. 32–A, No. 4, Oct. 1952, pp. 989–995.

Stainless Steel Drop-Forged Implant, Advertisement p. 54, Wright Mfg. Co., *The Journal of Bone and Joint Surgery*, vol. 46–A, No. 7, Oct. 1964.

*Primary Examiner*—Ronald L. Frinks
*Attorney, Agent, or Firm*—Theodore B. Roessel; James A. Rich

[57] ABSTRACT

A surgical implant is produced by coating a metallic substrate with enamel. The metallic substrate provides structural strength and the enamel provides chemical stability, resistance to wear, tissue compatibility, progressive ingrowth and electrical insulating properties. The implant may be produced by coating a portion of the metallic substrate with a partially crystallized enamel, and then positioning the implant on a firing support with the partially crystallized enamel in contact with the support and coating the remaining non-enamelled surface.

8 Claims, 9 Drawing Figures

U.S. Patent  Oct. 26, 1976  Sheet 1 of 2  3,987,499
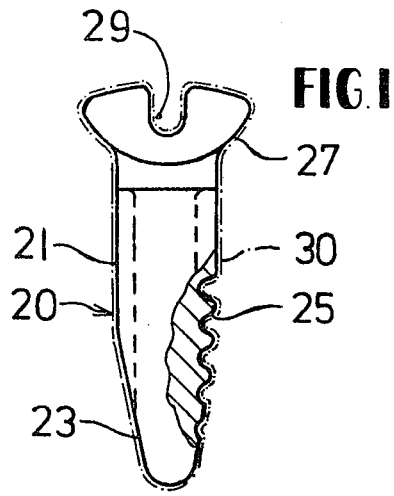
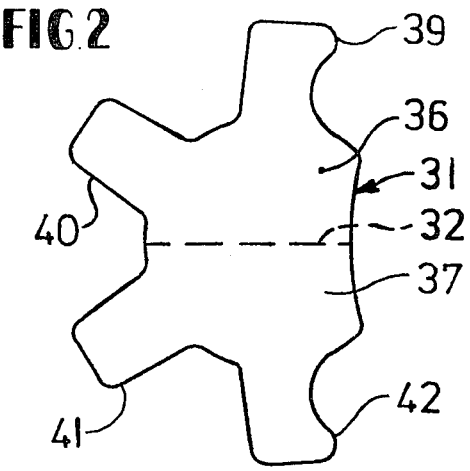
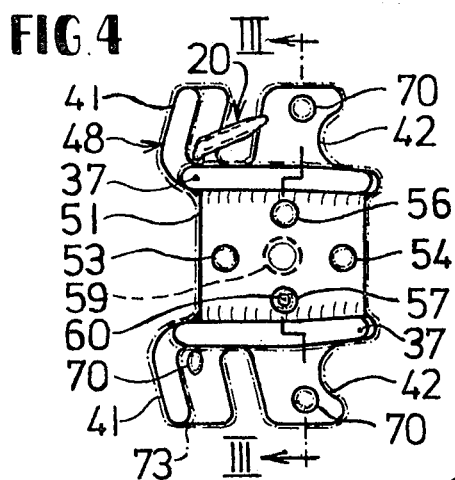
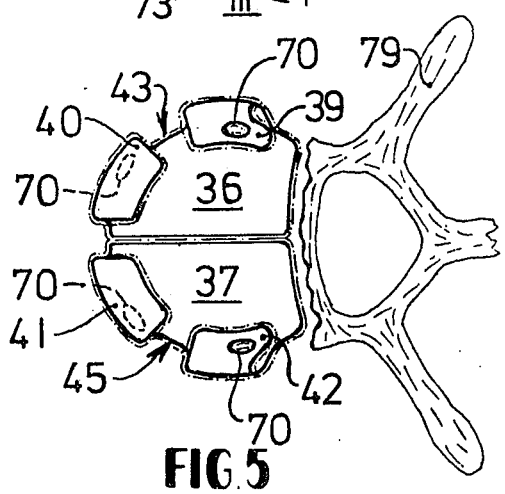
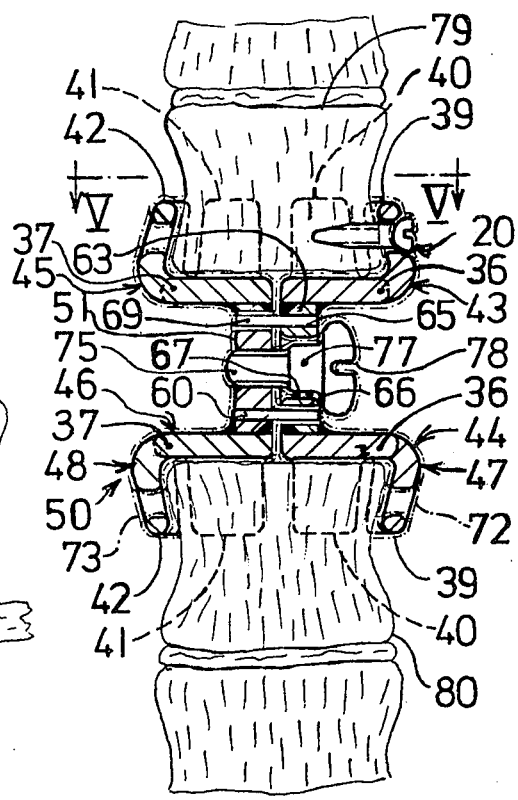

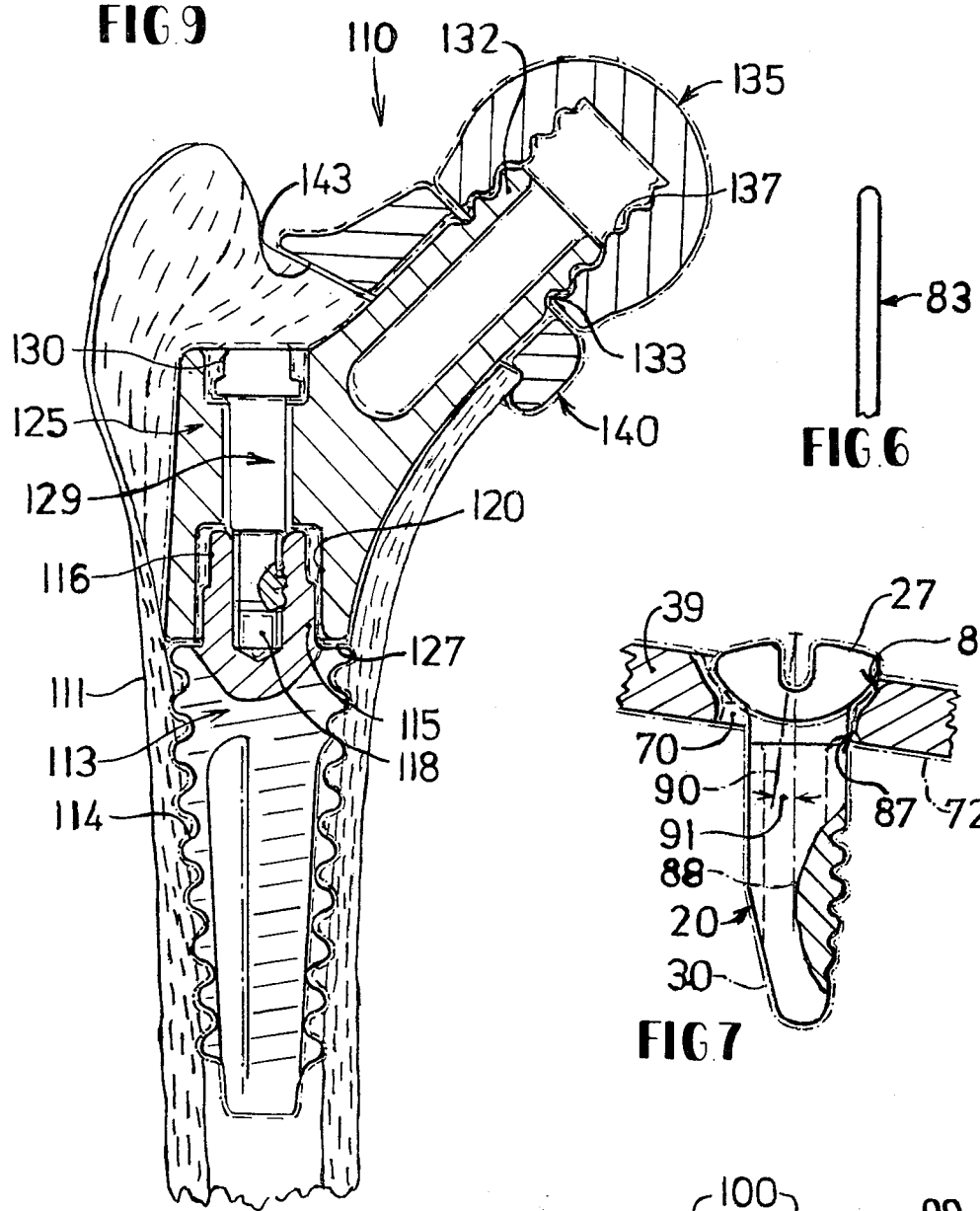

SURGICAL IMPLANT AND METHOD FOR ITS PRODUCTION

BACKGROUND OF THE INVENTION

This invention relates to metallic surgical implants, i.e., to metallic surgical construction elements which are intended to remain either permanently (endoprosthesis) or only temporarily in human or animal bodies.

Implants of this type have been made completely ("Contimet" Titan-Information, Ed. Hannover 1973) or partially (German Pat. No. 923,383) from metal. The drawback of these is the inadequate corrosion and stress-cracking resistance of the metals against the fluids and secretions of the living body as well as the insufficient abrasion resistance which results when parts of the implant slide relative to each other. The danger involved in metallic abrasion is that the abraded particles are carried into the surrounding tissues and become deposited therein. This may give rise to irritation and to the build up of connecting tissue which causes stiff joints. Also, this abrasion reduces the life expectancy of the implant, so that repeated operations may be required, particularly with younger patients. Several metallic implants in the body or foreign bodies with different electrochemical potential may lead, via the body fluids and secretions, to the formation of electrochemical circuits in the body.

Metallic implants may be anchored to the bones by means of bone cements based on methyl methacrylate. This cement has a tendency to polymerize and to shrink, whereby the rigid seating of the implant becomes lost. Furthermore, over long periods, monomers are spread within the body and may produce toxicity and circulatory difficulties.

Implants made from solid oxide ceramic without (British Pat. No. 1,083,769) or with (German Pat. No. 583,589) a glossy transparent mineral glaze are also known. The implants are given the glaze to produce a glossy surface when they are used as anatomical or panoptical models, but not when they are used for surgical purposes. The drawback of oxide ceramic implants is their relatively great brittleness and low fracture elongation, which means that they must be relatively large. Accordingly, their application is excluded where insufficient space is available. Also, the notch sensitivity of these material and the weight of implants manufactured therefrom are relatively high.

SUMMARY OF THE INVENTION

An object of this invention is to provide biocompatible and toxically satisfactory implants while insuring adequate strength, toughness and durability, and increasing the wear and corrosion resistance. Simultaneously, an enhanced construction freedom in the configuration of implants is achieved.

According to the invention, the implant comprises a metallic substrate at least partially coated with enamel. As used herein, the term enamel means a porcelain enamel, i.e., a vitreous or partially devitrified inorganic coating bonded to metal by fusion at a temperature above 800° F. The enamel can be a single layer or applied in a plurality of layers, e.g., with a ground coat next to the metallic substrate and one or more cover coats of enamel over the ground coat. The enamel can be applied over a variety of metals, such as high alloy steel or highly alloyed non-ferrous metals. The substrate metal can be adapted very exactly and reliably to special location circumstances, both as regards its configuration and as to its mechanical and physical properties. At the same time, the enamel can be selected with regard to optimum chemical stability, resistance to wear, tissue compatibility, progressive ingrowth (i.e., increasing incorporation or growing in of the implant with time) and electrical insulating properties. The enamel also forms a very firm bond with the base metal, which makes the implant safe for the patient.

Generally it is preferred to use a metal having relatively good chemical durability. This insures that the effects of bodyily contact with the metallic substrate will be slight if a pore in the enamel is penetrated or if a portion of the enamel is worn away after long mechanical stressing.

It is also preferable to use a metal having a low linear coefficient of expansion, e.g., $110-140 \times 10^{-7}/°C$ between 20° and 400° C. Implants are frequently relatively small articles with numerous and often very small radii. Typical examples are connecting and self-tapping screws, which are normally not enamelled. Sharp edges or corners can thus occur which cannot be taken off for constructional or operational reasons. Enamel coatings are normally applied so that they are under compressive stress. Over convex, very small curvatures, this leads to forces in the enamel layer perpendicular to the surface which can cause spalling of the enamel. This risk is minimized by matching the coefficient of expansion of the base metal to that of the enamel, so that the compressive stresses in the enamel can be reduced. The smaller the curvatures occuring in the implants, the lower the coefficients of expansion should be for the metallic substrate. Two examples of metals which substantially define the preferred range of linear coefficients of expansion are the materials known as Numbers 1.4762 and 2.4631 according to DIN 17007. These are the materials X 10 Cr Al 24 and Ni Cr 20 Ti Al according to DIN 17006.

In some embodiments of this invention the enamel may be partially devitrified or crystallized. Enamels of this type, some of which are disclosed in German Published Specification No. 1,291,597 and U.S. Pat. No. 3,368,712, have outstanding mechanical and physical characteristics. These crystallized enamels can be applied in several layers and, if desired, can be applied only to a portion of the metallic substrate.

With multi-layer applications the enamel can have a partially crystallized enamel ground coat on the base metal. These partially crystallized ground coats produce a firm adhesion between the base metal and enamel. With multi-layer application, the implant can also have a vitreous cover coat of enamel. In this way, with frictionally stressed implant parts, a better sliding behaviour can be obtained. The microscopic roughness which may be present on the surface of the partially crystallized enamel under the cover enamel can thus be avoided by a relatively thin vitreous enamel covering layer which, by its flame polishing and relatively low modulus of elasticity, insures the best break-in conditions for frictionally stressed implant parts.

The enamel surface may be profiled locally, e.g. by mechanical or chemical roughening or by the cutting of grooves or recesses. In this way, ingrowth or growing in of the implant into the body can be promoted and facilitated. The ground or cut recesses can have a diameter of 1 mm, for example, and, in relatively thick enamel layers, can be 1 mm deep. The centers of adjacent recesses can be about 4–5 mm apart.

While in many applications a partial enameling of the metallic substrate is sufficient, the enameling of the entire surface of the implant is preferred. This excludes any contact between the body and metallic substrate and thus excludes the formation of electrochemical circuits. Also, a relative common base metal can be used, as long as those requirements are fully taken into account which the metal is to fulfill in the metal-enamel composite article. Thus, implants of relatively low cost can be made.

Another object of this invention is to provide a method for manufacturing a surgical implant wholly coated with enamel. The metallic substrate is partially coated with a partially crystallize enamel, the substrate is positioned on a firing support with the partially crystallized enamel in contact with the support, and the remaining non-enameled surface of the substrate is coated with enamel. For this remaining surface, either a partially crystallized enamel or a stable vitreous enamel can be used. If required, the remaining surface may also be provided with an enamel ground coat and one or more enamel cover coats. With this method, the otherwise customary firing supports or firing projections on the article to be enameled can be eliminated because the increase in the viscosity of the partially crystallize enamel is made use of following its crystallization. This increase in viscosity is such that the implant can be laid directly on the firing support, with the surface coated with the partially crystallized enamel in contact with the support, without the contact surface suffering damage in the subsequent enameling of the remaining surface of the implant.

A typical embodiment of the invention, namely a dorsal vertebra endoprosthesis, comprises two mutually connectible parts interconnectible with each other substantially along the main longitudinal plane of the prosthesis. Each part has two connecting portions attachable to two adjacent vertebrae and a connecting limb between the two connecting portions. Like all other implants according to the invention, the vertebra endoprosthesis can be manufactured either by welding or by casting construction methods. The implant can be made relatively easily and may be comparatively lightweight yet strong, particularly by welded construction. In the operation, or installation of the implant, the mounting and firm anchoring of the two implant parts to the adjacent vertebrae is carried out rapidly and safely.

According to a further embodiment of the invention, the two connecting limbs are mutually engageable by means of an enamelled screw which is arranged with a guide shaft on the head side in a through bore in one of the limbs and is screwed with a threaded part into a threaded bore in the other limb. This implant consists of relatively few parts. The screw can have rounded threads, in order to facilitate the enamelling, and can be secured in the threaded bore by bone cement, e.g., a methyl methacrylate composition. The two parts of the implant can be fixed relative to each other by at least one securing pin and can thus be secured against relative rotation.

According to a further embodiment of the invention, each connecting portion includes at least one aperture or recess for the reception of a bone screw screwed into the adjacent vertebra. Thus, a rigid connection and firm seating between the connecting portion and the vertebra is ensured. The bone screw can be provided with self-tapping threads, so that it itself cuts the internal thread in the bone in a boring of predetermined diameter previously made in the bone.

According to a further embodiment of the invention, one wall of the recess is made at least partially spherically concave and a head of the bone screw is made complementarily spherically convex. Thus, the surface pressure between the screw head and the wall of the recess remains within predeterminable limits even if there is an angle between the axes of the screw and of the recess. Thus, the risk of damage to the enamel is reduced.

According to another embodiment of the invention, each connecting portion has a platform facing the end of the adjacent vertebra and at least one projection on the platform for cooperating with a side surface of the vertebra. This solution is technically simple and thus very functionally reliable. It also serves to save weight. The platform and the projections can also define together an acute angle. This ensures that the projections engage the side surfaces of the vertebra. This gives a positive, very firm and safe connection between the implant and the vertebra. To facilitate mounting of the implant during the operation, at least one holding aperture for a holding tool is provided in at least one of the connecting limbs. The holding tool can be a relatively long probe or rod, e.g., of titanium or stainless steel, which the surgeon inserts into the holding aperture. In this way, the surgeon can exert holding forces upon the implant part first inserted into the body and thus prevent any undesirable movement of this implant part during the operation. Also, the probes or rods facilitate parallel engagement of the two implant parts.

In another embodiment of the invention, namely a hip joint endoprosthesis, with a shank and a ball connectible with this shank and cooperating with a socket, the shank is divided into an anchoring part and a transition part connectible therewith and the ball is connectible with the transition part.

It is known to secure hip joint endoprostheses with bone cement in the femur, or upper thigh bone. As already mentioned, there is always the risk of separation of the cement and thus release of the prosthesis. Thus, complications and pathological tissue reactions can occur. This disadvantage is avoided by the invention, in that the anchoring part is provided with an external thread which taps itself into the femur. Preferably, in order to facilitate enamelling, this thread is made as a rounded thread. The transition part is coupled with the anchoring part which is thus connected in a closely fitting and durably rigid way with the bone, by making optimum use of the internal space of the femur and producing for the ball a very stiff support construction having due regard to all likely requirements.

According to another aspect of the invention, the anchoring part has a guide pin that fits into a recess in the transition part, and the latter can be stressed against the anchoring part by a securing screw screwed into the guide pin. Thus, the transition part can be installed at any desired rotational angle with reference to the anchoring part and fixed in the desired position by the securing screw, which can be secured by bone cement.

According to another embodiment of the invention, the ball can be screwed onto the free end of the transition part. This provides for axial adjustment of the ball relative to the transition part. Securement of the thread can again be provided by means of bone cement.

According to a further embodiment of the invention, a supporting member can be located between the ball and the femur. The supporting member can engage circumferentially around the transition part and can be supported with its abutment surface, which faces away from the ball, upon a seating surface on the femur, which has previously been prepared by the surgeon and adapted to the shape of the supporting member. Thus, force transfer between the femur and the supporting member takes place over the largest possible surface area for the best possible imitation of the natural conditions of the head of the hip joint.

DRAWINGS

FIG. 1 is a partially sectioned view of a bone screw according to this invention.

FIG. 2 illustrates a stamped sheet metal part for the production of one portion of a dorsal vertebra endoprosthesis.

FIG. 3 is a sectional view through the vertebra endoprosthesis along lines III—III in FIG. 4.

FIG. 4 shows a part of this vertebra endoprosthesis in side elevation view.

FIG. 5 is a plan view of the prosthesis along line V-V in FIG. 3, with the vertebra partly omitted.

FIG. 6 shows a holding tool in side view.

FIG. 7 shows a bone screw according to FIG. 1 in the mounted state;

FIG. 8 is a diagrammatic view of a multi-layer enamel construction.

FIG. 9 is a longitudinal section through a hip joint prosthesis in finished mounted condition.

DETAILED DESCRIPTION

In FIG. 1 a bone screw 20 is shown with a cylindrical shank 21 and a forward cutting part 23 narrowing to a rounded tip. The bone screw 20 has a rounded screw thread 25 and a head 27 which is made spherically convex on the side adjacent the shank 21 and, on the other side, is provided with a slot 29 for the reception of a screwdriver.

The entire surface of the bone screw 20 is coated with enamel 30. For simplicity, this and other enamel coats are represented in the drawings by dotted lines. These enamel coats can be formed in the way previously mentioned either as single layers or as multiple layers.

FIG. 2 shows a stamped sheet metal element 31 which is slit through along the dotted line 32. This provides two platforms 36 and 37. Spaced projections 39, 40 and 41, 42 extend from each of the platforms 36 and 37.

The projections 39–42 can be bent either downwardly or upwardly from the flat position shown in FIG. 2. This produces connecting members 43–46 of the two parts 47 and 48 of a dorsal vertebral endoprosthesis 50.

A connecting limb 51 is welded to the platforms 37 of the part 48. The limb contains two holding apertures 53 and 54, two openings 56 and 57 and a threaded bore 59, best seen in FIG. 4. A securing pin 60 is firmly pressed into the aperture 57.

In a similar way, a connecting limb 63 is welded to the two platforms 36 of the part 47. Limb 63 is provided with holding apertures (not shown) corresponding to the apertures 53 and 54 of FIG. 4 and also with openings 65 and 66 and a through bore 67. A securing pin 69 is fixed in the opening 65.

Apertures 70, the shape of which is described in detail below in connection with FIG. 7, are provided in the projections 39–42. The apertures 70 are intended to receive bone screws 20 of the kind shown on an enlarged scale in FIG. 1.

The two parts 47 and 48 of the vertebra endoprosthesis 50 are coated over their entire surfaces with enamel 72 and 73, which can be applied either as a single layer or in multiple layers and also with locally differing thicknesses. The parts 47 and 48 are held in the mounted state, as shown in FIG. 3, by a screw 75, which is located with its guide shank 77 in the through bore 67 and screwed into threaded bore 59. Screw 75 is also coated over its entire surface with enamel 78.

As FIG. 4 shows, the platforms 37 of each part, e.g., 48, are not parallel or are not entirely parallel to one another, but if required are inclined to one another locally so as to correspond to the natural relative inclination of the adjacent vertebrae 79 and 80 (FIG. 3).

In FIG. 5, that part of the vertebra 79 is omitted which is connected with the connecting members 43 and 45. FIG. 5 also shows how the upper ends of the projections 39–42 are inclined inwardly and positively engage around and firmly hold the vertebra 79 in the clamped state (FIG. 3). This anchoring is further improved by bone screw 20.

In FIG. 6 a longitudinally extending rod-shaped holding tool 83 of stainless steel or titanium is shown, which slidably fits into the holding openings, e.g., 53 and 54.

In FIG. 7 an aperture 70 is shown in the projection 39, The wall 87 of aperture 70 is constructed at 89 so as to be spherically complementarily concave with the head 27 of the screw 20. The axis 88 of the screw 20 and the axis 90 of the aperture 70 can thus define between them an angle 91 without forming any edge or point contact between the screw 20 and the projection 39 with the risk of local damage of the enamel 30 or 72.

The operation preferably takes place with the patient in the lateral position. First, after preparation of the abutment surfaces of the adjacent vertebrae 79 and 80, the part 48 of the vertebra endoprosthesis 50 is inserted downwardly. Then the surgeon inserts one or two of the holding tools 83 (FIG. 6) with their ends into the holding apertures 53 and 54 and thus can prevent displacement of the part 48 from its desired position. Then the second part 47, with its holding apertures aligned with the openings 53, 54, is slid on the holding tools 83, guided along parallel to the first part 48 and then butted up to the first part 48, so that the securing pin 60 is inserted into opening 66 and the securing pin 69 into opening 56. Thus, parts 47 and 48 are fixed with respect to one another. The holding tools 83 are then removed and the screw 75 can be inserted by means of a screwdriver. Prior to this, some bone cement is applied in the threaded bore 59, which after insertion of the screw 75 hardens and thus secures the screw 75 against undesirable loosening or falling out. Finally, borings are made into the vertebrae 79 and/or 80 through the apertures 70 in one or more of the projections 40 and 41. Self-tapping bone screws 20 are screwed into these borings at an angle to the adjacent platform 36 or 37. The adjacent vertebrae 79 and 80 are thereby drawn firmly up to the associated platforms 36 and 37. For further securement, bone screws 20 can be inserted through the apertures 70 located in the projections 39 and 42, namely perpendicularly into the vertebrae 79 and 80. In this way, a positively firm and very rigid connection with the vertebrae 79 and 80 is given.

PREPARATIVE EXAMPLE

The parts 47, 48, made from the material identified by the number 2.4631 and are prepared in the usual way by pickling or sand blasting for the enamelling process. A crystallizable enamel composition according to Table I is melted, fritted, ground, applied, fired and finally subjected to controlled heat treatment so as to induce partial crystallization, in the way described in German Published Specification No. 1,291,597 and U.S. Pat. No. 3,368,712.

TABLE I

| Oxide | Weight percent of the total coating composition |
|---|---|
| $SiO_2$ | 56.02 |
| $Na_2O$ | 6.50 |
| $Li_2O$ | 10.38 |
| $Al_2O_3$ | 5.46 |
| $TiO_2$ | 16.60 |
| $B_2O_3$ | 4.50 |
| SrO | 1.50 |

The frit, prepared as slip, is preferably applied by spraying on the flat surfaces, particularly the platforms 36 and 37, more enamel is preferably applied then on the sides and edges. The enamel thickness on the supporting surfaces for the vertebrae 79 and 80 preferably amounts to 1 to 2 mm and over the edges is 0.2 to 0.3 mm, which is achieved after 2 to 3 firings. In the foregoing steps, enamel is not applied to the surfaces required for supporting or suspending the implant parts in the enamelling oven. After the enamel has been applied controlled crystallization is carried out. With the above-mentioned material, it is unnecessary to apply a ground coat under the crystallizable enamel, however, if such a ground coat is desired, it can have the composition corresponding to Table II below.

TABLE II

| Oxide | Weight Percent |
|---|---|
| $SiO_2$ | 48.5 |
| $Na_2O$ | 14.7 |
| $K_2O$ | 4.4 |
| $Al_2O_3$ | 6.4 |
| $MnO_2$ | 1.7 |
| $B_2O_3$ | 16.0 |

The article enamelled and partially crystallized except on the support surfaces is then tested for contact points with the metal substrate by means of a high potential (3 to 10 kV) or by the current measuring method after immersion in an electrolyte. If no fractures are found, the fired region is mechanically cleaned and then treated with an enamel slip, e.g., according to Table I. In the then-repeated firing and crystallization processes, the article is supported with the already partially crystallized enamel coat upon a non-oxidizing support.

The screw 75 can be made of high-alloy steel with the material number 1.4762 and can be enamelled over its entire surface according to the above-described method.

In the case of the parts 47 and 48, the enamelling can also be carried out according to a known method in which the parts are suspended and enamelled upon an extension of the securing pins 60 and 69 which are no longer present as these are shown in FIG. 3. The extensions are then removed and the free ends of the securing pins 69 and 60 are likewise enamelled by local heating and melting in a tube furnace.

In FIG. 8, a multilayer construction is illustrated by way of example. An enamel ground coat 96, two intermediate enamel coats 97 and 98 of partially crystallized enamel and a vitreous enamel cover coat 99 are located in that order on a metal substrate 95. Depressions or recesses 100 are ground or otherwise cut or made in the enamel at mutually spaced locations which improve growing in of the implant into the body.

As the enamel cover coat 99, the four known highly acidresistant enamels shown in Table III below can be used.

TABLE III

| | 1 | 2 | 3 | 4 |
|---|---|---|---|---|
| $SiO_2$ | 65.1 | 66.9 | 51.1 | 65.3 |
| $Al_2O_3$ | 3.5 | 3.0 | 2.6 | 3.1 |
| $B_2O_3$ | 2.0 | — | 9.4 | — |
| $K_2O$ | 2.6 | } 18.7 | 1.3 | 1.5 |
| $Na_2O$ | 19.1 | | 17.3 | 18.1 |
| CaO | 7.7 | 7.3 | 6.5 | 6.9 |
| MgO | — | — | — | 5.1 |
| ZnO | — | 1.1 | 11.8 | — |
| $Li_2O$ | — | 3.0 | — | — |

FIG. 9 shows a hip joint endoprosthesis 110. An anchoring part 113 with a self-tapping external rounded screw thread 114 is screwed into a femur or upper thigh bone 111. At the top, the anchoring part 113 carries a boss or guide pin 115 of essentially annular cross-section. At its upper end only, the guide pin 115 has two diametrically opposite flat lateral surfaces 116 which a tool, e.g., a box spanner, can engage for inserting and, if required, removing the anchoring part 113. A central threaded blind hole 118 is also provided in the guide pin 115.

Above the guide pin 115, a transition part 125 with a downward recess 120 is located, which sits with its lower edge upon a shoulder 127 formed on the anchoring part 113. A securing screw or bolt 129 has two diametrically opposite flats 130 on its otherwise cylindrical head, by means of which a tool can be applied for inserting and removing the securing screw 129.

The free end 132 of the transition part 125 is made hollow to save weight and is also provided with an external rounded thread 133 on which a ball 135 with an internal rounded thread 137 can be screwed. Between the ball 135 and the femur 111, a supporting member 140 is held and bears with its lower surface 143 over the largest possible area of a corresondingly prepared counter-surface made on the femur 111.

As the dotted external contours show, all the individual parts of the hip joint endoprosthesis 110 described are coated over their entire surfaces with enamel, so that the base metal is not exposed anywhere.

The securing screw 129 and the ball 135 are secured to their complementary screw threads by means of a small amount of bone cement.

Thus, it may be seen that this invention provides implants that are biocompatible, toxically satisfactory, strong, tough, durable, easily manufactured, and possessing increased wear and corrosion resistance. Furthermore, these implants can easily be tailored to the requirements of specific problems. Of course, the implants described above are but two of many possible embodiments falling within the scope of this invention, which is defined by the following claims.

We claim:

1. A metallic hip joint prosthesis at least partially coated with enamel, comprising a transition part having a recess, an anchoring part having a guide pin which is inserted in said recess, said transition part being fastened to said anchoring part with a securing screw which is screwed into said guide pin, and a ball connected to said transition part, said ball being adapted to cooperate with a socket.

2. A prosthesis according to claim 1 wherein the transition part has an external thread, the ball has an internal thread, and the ball is screwed onto the transition part.

3. A metallic vertebra prosthesis at least partially coated with enamel, comprising:
    two parts interconnectible with each other substantially along the main longitudinal plane of the prosthesis, each of said parts comprising:
        two connecting portions connectible to adjacent vertebrae, each of said connecting portions having a platform adapted to face the end of an adjacent vertebra and at least one projection adapted to engage a lateral surface of the vertebra; and
        a connecting limb between the two connecting portions of said part.

4. A prosthesis according to claim 3 wherein the connecting limb of one of said parts contains a through bore, the connecting limb of the other part contains a threaded bore, and the two parts are connected to each other by one enameled screw that has a quide shank that extends through said through bore and is screwed into said threaded bore.

5. A prosthesis according to claim 4 wherein said enameled screw is secured in said threaded bore by bone cement.

6. A prosthesis according to claim 3 wherein each of said connecting limbs contains at least one opening and the two parts are fixed relative to one another by at least one securing pin extending through said openings.

7. A prosthesis according to claim 3 wherein said platform and said projection define an acute angle.

8. A prosthesis according to claim 3 wherein at least one of said connecting limbs is provided with at least one holding opening for insertion of a holding tool.

* * * * *